United States Patent [19]

Jannard

[11] 4,447,914
[45] May 15, 1984

[54] GOGGLE

[75] Inventor: James H. Jannard, Laguna Niguel, Calif.

[73] Assignee: Oakley, Inc., Irvine, Calif.

[21] Appl. No.: 341,846

[22] Filed: Jan. 22, 1982

[51] Int. Cl.³ ............................................. A61F 9/02
[52] U.S. Cl. .......................................... 2/432; 2/436; 2/439
[58] Field of Search .................. 2/432, 436, 437, 439, 2/435, 8, 9, 440, 441

[56] References Cited

U.S. PATENT DOCUMENTS

| 2,545,078 | 3/1951 | Gardner | 2/432 X |
| 2,573,722 | 11/1951 | Maurer et al. | 2/437 |
| 3,945,044 | 3/1976 | McGee et al. | 2/436 |
| 4,150,443 | 4/1979 | McNeilly | 2/436 |

Primary Examiner—Peter P. Nerbun
Attorney, Agent, or Firm—William W. Haefliger

[57] ABSTRACT

A flexible goggle has an internal frame ledge with antiglare textured surface.

3 Claims, 4 Drawing Figures

U.S. Patent  May 15, 1984  4,447,914
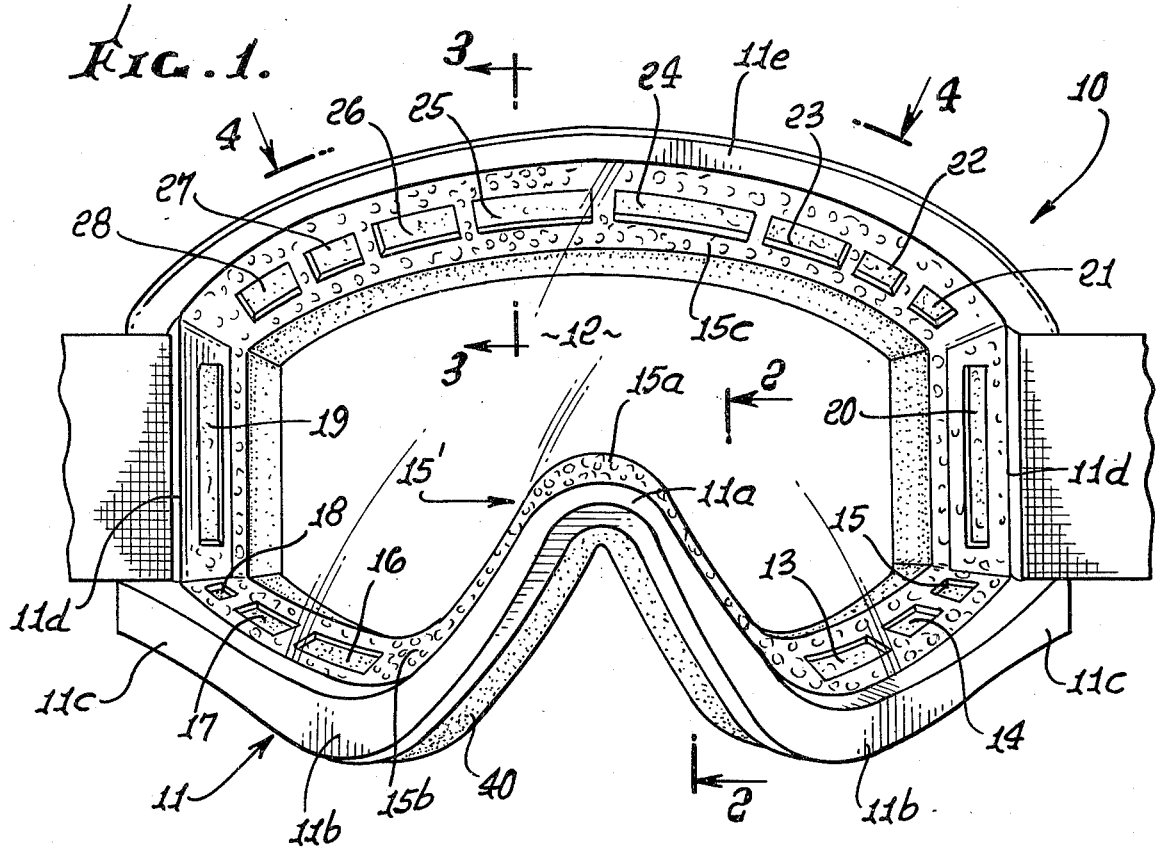
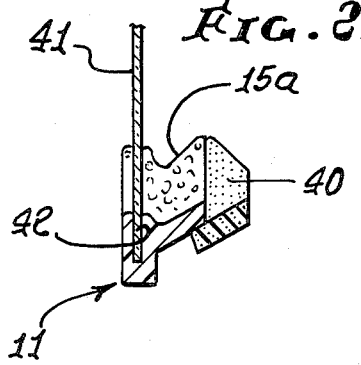
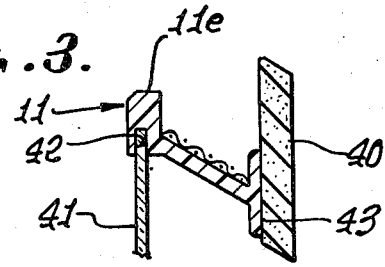
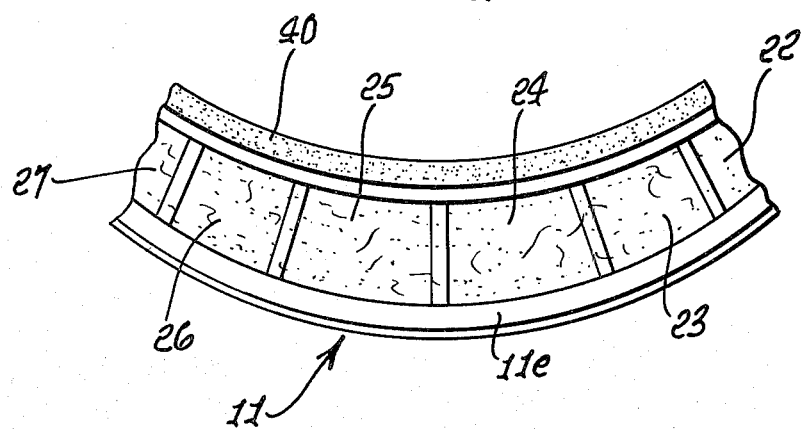

GOGGLE

BACKGROUND OF THE INVENTION

This invention relates generally to goggles, and more particularly to anti-glare goggles.

There is a need for flexible goggles which minimize glare, and particularly internal glare produced when light enters the goggle lens and impinges on the frame. Flexible goggles are typically worn by bicycle and motorcycle riders.

SUMMARY OF THE INVENTION

It is a major object of the invention to meet the above need, in a practical and useful manner. Basically, the goggle includes:

(a) a forwardly facing flexible frame,
(b) a forwardly convex flexible lens carried by the frame,
(c) the frame having a ledge located rearwardly of the lens,
(d) the ledge having a textured surface to reduce glare of light passing through the lens and incident on said ledge.

Further, the textured surface slants away from the eyes of the user, at critical location, as will appear.

These and other objects and advantages of the invention, as well as the details of an illustrative embodiment, will be more fully understood from the following specification and drawings in which:

DRAWING DESCRIPTION

FIG. 1 is a frontal view of a goggle;
FIG. 2 is a section on lines 2—2 of FIG. 1;
FIG. 3 is a section on lines 3—3 of FIG. 1; and
FIG. 4 is a plan view of lines 4—4 of FIG. 1.

DETAILED DESCRIPTION

In the drawings, the goggle 10 has a flexible plastic frame 11, with an upwardly humped nose bridge middle portion 11a, downwardly convex lower extents 11b laterally of portion 11a, upwardly and outwardly inclined side extents 11c, vertical extents 11d, and arching upper extent 11e joined to vertical extents 11d.

Air venting openings through the frame, and extending in direction away from the center zone 12, appear at 13-15, 16-18, 19, 20 and 21-28.

A polyurethane foam (or equivalent cushion 40 conforms to the above described shape of the frame, and is attached to the rear side thereof, as at 43 in FIG. 3. Note also that the frame is forwardly convex and rearwardly concave (see FIG. 4).

A thin, plastic, flexible lens 41 is carried by the frame, as by frame grooving 42 sunk in all of the frame portions described above.

The frame has a ledge 15' located rearwardly of the lens, and that ledge has a textured (i.e. roughened or dimpled anti-glare) exposed surface, to reduce glare of light passing through the lens and incident on that ledge. The textured surface has upwardly humped extent 15a which is forwardly and downwardly inclined above and laterally of the nose bridge; and the textured surface has forwardly and downwardly inclined side extents 15b laterally of the humped extent. Thus, the wearer can look down and forwardly, without glare difficulty.

Further, the textured surface has overlying extent 15c spaced above the extents 15a and 15b, and slanting forwardly and upwardly, so that the wearer can look upwardly and forwardly without glare problems. Finally vertical textured surfaces extend about vertical opening 19 and 20, as shown. The vent openings intersect the textured surface extents, as shown.

I claim:

1. In a goggle, the combination comprising
(a) a forwardly facing flexible frame,
(b) a forwardly convex flexible eye protecting lens carried by the frame,
(c) the frame having a ledge located rearwardly of the lens and extending about and adjacent the space immediately rearwardly of the lens,
(d) the ledge having a textured surface to reduce glare of light passing through the lens and incident on said ledge, said surface inclined relative to the lens to flare forwardly toward and openly face the lens,
(e) said textured surface having upwardly humped extent which is forwardly and downwardly inclined above and laterally of a nose bridge defined by the frame.

2. The combination of claim 1 wherein the frame has air venting through openings intersecting said textured surface.

3. The combination of claim 1 wherein the textured surface has overlying extent spaced above said humped extent and said side extents.

* * * * *